(12) United States Patent  
Seckar (10) Patent No.: US 8,760,644 B2  
(45) Date of Patent: Jun. 24, 2014

(54) SYSTEMS AND METHODS FOR CLEANING AN INLINE OPTICAL FLUID ANALYZER

(71) Applicant: Halliburton Energy Services, Inc., Houston, TX (US)

(72) Inventor: Charles Seckar, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 13/664,845

(22) Filed: Oct. 31, 2012

(65) Prior Publication Data

US 2014/0116120 A1    May 1, 2014

(51) Int. Cl.
```
G01N 21/01    (2006.01)
G01N 1/10     (2006.01)
G01N 21/03    (2006.01)
G01N 21/05    (2006.01)
```

(52) U.S. Cl.  
CPC ................. *G01N 21/03* (2013.01); *G01N 21/05* (2013.01)  
USPC .......................................... 356/244; 356/246

(58) Field of Classification Search  
CPC ....... G01N 21/553; G01N 21/03; G01N 21/05  
USPC .................................................. 356/445–448  
See application file for complete search history.

(56) References Cited

U.S. PATENT DOCUMENTS

| | | | |
|---|---|---|---|
| 5,104,228 A * | 4/1992 | Baillie ........................... | 356/442 |
| 5,153,671 A * | 10/1992 | Miles ............................ | 356/301 |
| 5,822,058 A * | 10/1998 | Adler-Golden et al. ...... | 356/303 |
| 6,198,531 B1 | 3/2001 | Myrick et al. | |
| 6,529,276 B1 | 3/2003 | Myrick | |
| 6,867,861 B2 * | 3/2005 | Martino et al. ............... | 356/319 |
| 7,123,844 B2 | 10/2006 | Myrick | |
| 7,834,999 B2 | 11/2010 | Myrick et al. | |
| 7,911,605 B2 | 3/2011 | Myrick et al. | |
| 7,920,258 B2 | 4/2011 | Myrick et al. | |
| 8,049,881 B2 | 11/2011 | Myrick et al. | |
| 8,208,147 B2 | 6/2012 | Myrick et al. | |
| 8,358,418 B2 | 1/2013 | Myrick et al. | |

(Continued)

FOREIGN PATENT DOCUMENTS

| | | |
|---|---|---|
| WO | 01-31328 A1 | 5/2001 |
| WO | 2014070864 A1 | 5/2014 |

OTHER PUBLICATIONS

International Search Report and Written Opinion for PCT/US2013/067458 dated Feb. 17, 2014.

*Primary Examiner* — Michael P Stafira  
(74) *Attorney, Agent, or Firm* — McDermott Will & Emery LLP; John W. Wustenberg (57) ABSTRACT

Disclosed are systems and methods for cleaning optical windows used in an inline optical fluid analyzer. One system includes a sampling module having an inlet and an outlet and a flow path extending therebetween, the flow path being fluidly coupled to a pipeline containing a fluid, at least one optical computing device arranged within the sampling module in optical communication with the flow path and configured to monitor a sample flow of the fluid for one or more characteristics of the fluid, the at least one optical computing device having one or more optical sampling windows in contact with the sample flow of the fluid, and a solvent dispenser fluidly coupled to the flow path and configured to provide a solvent to the flow path to remove a residue built up on the one or more sampling windows.

21 Claims, 2 Drawing Sheets

(56) References Cited

U.S. PATENT DOCUMENTS

| | | | |
|---|---|---|---|
| 2002/0167663 A1* | 11/2002 | Martino et al. | 356/319 |
| 2005/0168736 A1* | 8/2005 | Slater | 356/301 |
| 2009/0046287 A1* | 2/2009 | Haught et al. | 356/319 |
| 2010/0097605 A1* | 4/2010 | Murakami et al. | 356/337 |
| 2010/0228688 A1* | 9/2010 | Little et al. | 705/413 |
| 2011/0102790 A1* | 5/2011 | Haught et al. | 356/319 |
| 2012/0000643 A1 | 1/2012 | Bruun et al. | |
| 2012/0074110 A1 | 3/2012 | Zediker et al. | |
| 2012/0118568 A1 | 5/2012 | Kleefisch et al. | |
| 2012/0150451 A1 | 6/2012 | Skinner et al. | |

* cited by examiner

SYSTEMS AND METHODS FOR CLEANING AN INLINE OPTICAL FLUID ANALYZER

BACKGROUND

The present invention relates to systems and methods of monitoring a fluid and, more specifically, to systems and methods for cleaning optical windows used in an inline optical fluid analyzer.

In the oil and gas industry, it can be important to precisely know the characteristics and chemical composition of fluids circulating into and out of subterranean hydrocarbon-bearing formations. The analysis of such fluids can be conducted off-line using laboratory analyses, such as spectroscopic and/or wet chemical methods, which analyze an extracted sample of the fluid. Depending on the analysis required, however, such an approach can take hours to days to complete, and even in the best case scenario, a job will often be completed prior to the analysis being obtained. While such retrospective analyses can be satisfactory in certain cases, they nonetheless do not allow real-time or near real-time analysis capabilities.

Real-time monitoring of fluids can be of considerable interest in order to monitor how the fluids change over time, thereby providing an operator with a real time determination of the exact contents in a flow line or pipeline. For example, various adulterants and/or contaminants may be present within the fluids, such as waxes, paraffins, asphaltenes, water, etc. Such contaminants can lead to harmful scale formation, impurity buildup, and bacterial growth, all of which can impede processes in which the fluid is used, and even damage process equipment in certain cases. Know the particular contents of a fluid flow and their relative concentrations in real-time may allow an operator to proactively manage the fluid flow and maximize production capabilities.

In some applications, inline optical devices have been used to monitor a fluid in a flow line or pipeline in order to determine particular properties or characteristics of the fluid. Such optical devices are often equipped with sensor assemblies including an optical window through which measurements are made as a function of reflectance, transmittance, fluorescence, or another optical or photosensitive response. At least one difficulty encountered with inline optical devices is the fouling of the optical window, which limits the accuracy and testing capabilities of the optical device. One way to remove the film or residue built up on the optical window is to disassemble the optical device and physically clean or wipe the optical window. Such a process, however, can be quite time-consuming, and in aggressive fouling environments, this may require an excessive amount of disassembly and cleaning.

SUMMARY OF THE INVENTION

The present invention relates to systems and methods of monitoring a fluid and, more specifically, to systems and methods for cleaning optical windows used in an inline optical fluid analyzer.

In some embodiments, an inline optical fluid analyzer is disclosed. The analyzer may include a sampling module having an inlet and an outlet and a flow path extending therebetween, the flow path being fluidly coupled to a pipeline containing a fluid, at least one optical computing device arranged within the sampling module in optical communication with the flow path and configured to monitor a sample flow of the fluid for one or more characteristics of the fluid, the at least one optical computing device having one or more optical sampling windows in contact with the sample flow of the fluid, and a solvent dispenser fluidly coupled to the flow path and configured to provide a solvent to the flow path to remove a residue built up on the one or more sampling windows.

In other embodiments, a method of operating an inline optical fluid analyzer may be disclosed. The method may include directing a sample flow of a fluid to a flow path defined within a sampling module having an inlet and an outlet, the flow path extending between the inlet and the outlet, analyzing the sample flow of the fluid for one or more characteristics with at least one optical computing device arranged within the sampling module and having one or more optical sampling windows in contact with the sample flow of the fluid, providing a solvent to the flow path from a solvent dispenser fluidly coupled to the inlet, and at least partially removing a residue built up on the one or more sampling windows with the solvent.

In yet other embodiments, a method of cleaning an inline optical fluid analyzer may be disclosed. The method may include flowing a fluid through a flow path defined in a sampling module having an inlet and an outlet, the flow path extending between the inlet and the outlet, analyzing the fluid with at least one optical computing device arranged in optical communication with the fluid and having one or more optical sampling windows in contact with the fluid, providing an output signal corresponding to one or more characteristics of the fluid with the at least one optical computing device, and initiating a window cleaning treatment by providing a solvent to the flow path to remove a residue built up on the one or more sampling windows, the solvent being injected into the flow path from a solvent dispenser fluidly coupled to the inlet.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present invention relates to systems and methods of monitoring a fluid and, more specifically, to systems and methods for cleaning optical windows used in an inline optical fluid analyzer.

The exemplary systems and methods described herein are used in conjunction with one or more optical computing devices, also commonly referred to as "opticoanalytical devices," for the real-time monitoring of a fluid. In operation, the optical computing devices may be useful and otherwise advantageous in determining the quality of the fluid, including determining the concentration of one or more chemical constituents or substances flowing within the fluid or otherwise forming an integral part thereof. Knowing the chemical makeup or other parameters of the fluid may provide an operator with valuable information relating to a deliverable product to a customer. Moreover, such data may allow the operator to proactively control the fluid flow, such as by initiating one or more remedial treatments configured to counteract an adulterant or other contaminant present in the fluid.

The optical computing devices may include one or more optical sampling windows in fluid communication with the fluid and used to obtain optical measurements of the fluid as a function of reflectance, transmittance, fluorescence, or another optical or photosensitive response. When the sampling windows eventually become fouled via film or residue buildup thereon, the systems and methods described herein further provide a window cleaning system configured to introduce or otherwise provide a solvent designed to dissolve or otherwise remove the residue from the sampling windows. Once the cleaning treatment is completed, the optical computing devices may be able to determine whether the cleaning treatment was successful by comparing the output signals with a normalized output signal. If the cleaning treatment was not entirely successful, an additional cleaning treatment may be required or otherwise the optical computing devices may be recalibrated to take into account the output signal variations detected.

Those skilled in the art will readily appreciate that the systems and methods disclosed herein may be suitable for use in the oil and gas industry since the optical computing devices provide a cost-effective, rugged, and accurate means for monitoring hydrocarbon quality, and the associated cleaning system helps to facilitate the efficient monitoring and management of oil/gas production. It will be further appreciated, however, that the various disclosed systems and methods are equally applicable to other technology or industry fields including, but not limited to, the food, medical, and drug industries, industrial applications, pollution mitigation, recycling industries, mining industries, security and military industries, or any field where it may be advantageous to determine real-time characteristics of a fluid within a flow path. In at least one embodiment, for example, the present systems and methods may be employed to monitor and regulate the quality of potable water.

As used herein, the term "fluid" refers to any substance that is capable of flowing, including particulate solids, liquids, gases, slurries, emulsions, powders, muds, combinations thereof, and the like. In some embodiments, the fluid can be an aqueous fluid, including water or the like. In other embodiments, the fluid can be a non-aqueous fluid, including organic compounds and, more specifically, hydrocarbons, oil, a refined component of oil, petrochemical products, and the like. In some embodiments, the fluid can be a treatment fluid or a formation fluid as found in the oil and gas industry. Fluids can include various flowable mixtures of solids, liquids and/or gases. Illustrative gases that can be considered fluids according to the present embodiments include, for example, air, nitrogen, carbon dioxide, argon, helium, methane, ethane, butane, and other hydrocarbon gases, combinations thereof and/or the like.

As used herein, the term "characteristic" refers to a chemical, mechanical, or physical property of a substance, such as a fluid or a substance present within the fluid. A characteristic of a substance may include a quantitative value of one or more chemical components therein. Such chemical components may be referred to herein as "analytes." Illustrative characteristics of a substance that can be monitored with the optical computing devices disclosed herein can include, for example, chemical composition (e.g., identity and concentration in total or of individual components), impurity content, pH, viscosity, density, ionic strength, total dissolved solids, salt content, porosity, opacity, bacteria content, combinations thereof, and the like. Moreover, the phrase "characteristic of interest of/in a fluid" may be used herein to refer to the characteristic of a substance contained in or otherwise flowing with the fluid.

As used herein, the term "flow path" refers to a route through which a fluid is capable of being transported between two points. In some cases, the flow path need not be continuous or otherwise contiguous between the two points. Exemplary flow paths include, but are not limited to, a flow line, a pipeline, a hose, a storage vessel, a trough, a stream, a sewer, a subterranean formation, etc., combinations thereof, or the like. In cases where the flow path is a pipeline, or the like, the pipeline may be a pre-commissioned pipeline or an operational pipeline. It should be noted that the term "flow path" does not necessarily imply that a fluid is flowing therein, rather that a fluid is capable of being transported or otherwise flowable therethrough.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation from a fluid, or a substance within the fluid, and produce an output of electromagnetic radiation from a processing element arranged within the optical computing device. The processing element may be, for example, an integrated computational element (ICE) used in the optical computing device, but may refer to any other processing element known to those skilled in the art. As discussed in greater detail below, the electromagnetic radiation that optically interacts with the processing element is changed so as to be readable by a detector, such that an output of the detector can be correlated to at least one characteristic of the fluid. The output of electromagnetic radiation from the processing element can be reflected electromagnetic radiation, transmitted electromagnetic radiation, and/or dispersed electromagnetic radiation.

As used herein, the term "optically interact" or variations thereof refers to the reflection, transmission, scattering, diffraction, or absorption of electromagnetic radiation either on, through, or from one or more processing elements (i.e., integrated computational elements). Accordingly, optically interacted light refers to light that has been reflected, transmitted, scattered, diffracted, or absorbed by, emitted, or re-radiated, for example, using the integrated computational elements, but may also apply to interaction with a fluid or a substance within the fluid.

Figure 1:
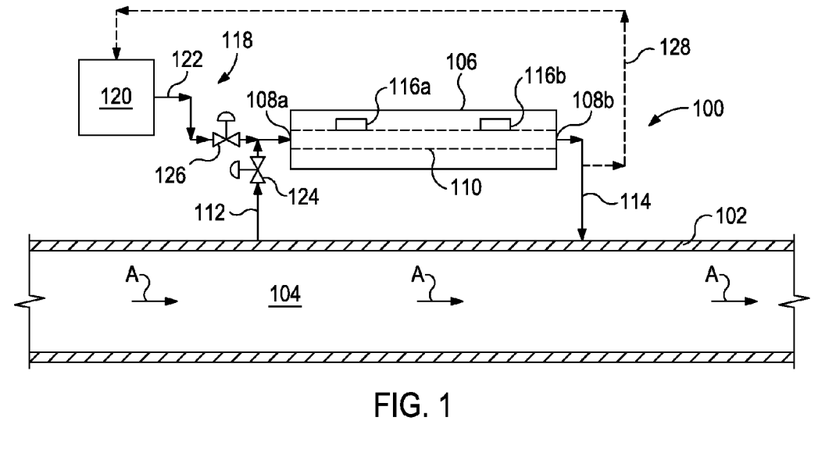
FIG. 1 illustrates an exemplary inline optical fluid analyzer, according to one or more embodiments.

Referring to FIG. 1, illustrated is an exemplary inline optical fluid analyzer 100, according to one or more embodiments. In some embodiments, the analyzer 100 may be fluidly coupled to a flow line or pipeline 102 which contains a fluid 104 therein. As illustrated, the pipeline 102 may be configured to convey or otherwise transport the fluid 104 therein generally in the direction indicted by the arrows A. In at least one embodiment, the fluid 104 may be a hydrocarbon, such as crude oil, and the pipeline 102 may be fluidly coupled at one end (e.g., to the left in FIG. 1) to a well head (not shown). In operation, the pipeline 102 may be configured to convey the fluid 104 to a downstream processing or storage facility (not shown), such as a refinery, a storage tank or vessel, or a transport vehicle.

The analyzer 100 may include a sampling module 106 having an inlet 108a and an outlet 108b fluidly coupling the sampling module 106 to the pipeline 102. The sampling module 106 may define a flow path 110 extending between the inlet 108a and the outlet 108b, and the fluid 104 from the pipeline 102 may be provided to the flow path 110 via a first conduit 112 fluidly coupled to the inlet 108a. Specifically, the first conduit 112 may be configured to extract of a sample flow of the fluid 104 to be delivered to the sampling module 106 for analysis. After traversing the length of the flow path 110, the sample flow of the fluid 104 may exit the sampling module 106 at the outlet 108b which returns the fluid 104 to the pipeline 102 via a second conduit 114.

In order to monitor or otherwise analyze the sample flow of the fluid 104, the analyzer 100 may further include one or more optical computing devices 116 (shown 116a and 116b) arranged or otherwise disposed within the sampling module 106 and in optical communication with the flow path 110. As illustrated, the optical computing devices 116a,b may be arranged along or in the flow path 110 in order to monitor the fluid 104 as it flows therethrough. While two optical computing devices 116a,b are illustrated in FIG. 1, it will be appreciated that any number of optical computing devices 116 (even one) may be employed in the inline optical fluid analyzer 100, without departing from the scope of the disclosure. For instance, the first and second optical computing devices 116a,b may be configured to provide redundant monitoring data for the fluid 104 such that the analyzer 100 may be configured to properly function with only one of the first or second optical computing devices 116a,b in the event the other fails or is otherwise rendered inoperable.

The exemplary optical computing devices 116a,b may be specifically configured for detecting, analyzing, and quantitatively measuring a particular characteristic or analyte of interest of the fluid 104 in the flow path 110, such that an operator may be apprised of the exact chemical and physical parameters of the fluid 104 flowing within the pipeline 102. In other embodiments, the optical computing devices 116a,b may be general purpose optical devices, with post-acquisition processing (e.g., through computer means) being used to specifically detect the characteristic of the fluid 104.

Suitable structural components for the optical computing devices 116a,b are described in commonly owned U.S. Pat. Nos. 6,198,531; 6,529,276; 7,123,844; 7,834,999; 7,911,605, 7,920,258, and U.S. Pat. No.8,049,881, each of which is incorporated herein by reference in its entirety, and U.S. patent application Ser. Nos. 12/094,460; 12/094,465; and 13/456,467, each of which is also incorporated herein by reference in its entirety. As will be appreciated, variations of the structural components of the optical computing devices described in the above-referenced patents and patent applications may be suitable, without departing from the scope of the disclosure, and therefore, should not be considered limiting to the various embodiments or uses disclosed herein.

The optical computing devices 116a,b can perform calculations (analyses) in real-time or near real-time without the need for time-consuming sample processing. Moreover, the optical computing devices 116a,b can be specifically configured to detect and analyze a particular characteristic of interest of the fluid 104. As a result, interfering signals are discriminated from those of interest in the fluid 104 by appropriate configuration of the optical computing devices 116a,b, such that a rapid response regarding the characteristics of the fluid 104 as based on the detected output is provided. In some embodiments, the detected output can be converted into a voltage that is distinctive of the magnitude of the characteristic being monitored in the fluid 104.

In some embodiments, the optical computing devices 116a,b can be configured to detect not only the composition and concentrations of a chemical constituent or compound present in the fluid 104, but they also can be configured to determine physical properties and other characteristics of the fluid 104, based on their analysis of the electromagnetic radiation received from the fluid 104. As will be appreciated, the optical computing devices 116a,b may be configured to detect as many characteristics of the fluid 104 as desired, all that is required to accomplish this is the incorporation of suitable processing and detection means within each optical computing device 116a,b for each characteristic.

The optical computing devices 116a,b may utilize electromagnetic radiation to perform calculations, as opposed to the hardwired circuits of conventional electronic processors. When electromagnetic radiation interacts with the fluid 104, unique physical and chemical information about the fluid 104 may be encoded in the electromagnetic radiation that is reflected from, transmitted through, or radiated from the fluid 104. This information is often referred to as the spectral "fingerprint" of the fluid 104 or the chemical compound present therein. The optical computing devices 116a,b may be capable of extracting the information of the spectral fingerprint of multiple characteristics or analytes within the fluid 104, and converting that information into a detectable output relating to one or more properties of the fluid 104. That is, through suitable configurations of the optical computing devices 116a,b, electromagnetic radiation associated with a characteristic or analyte of interest can be separated from electromagnetic radiation associated with all other components of the fluid 104 in order to estimate the properties of the chemical compound of interest in real-time.

Figure 2:
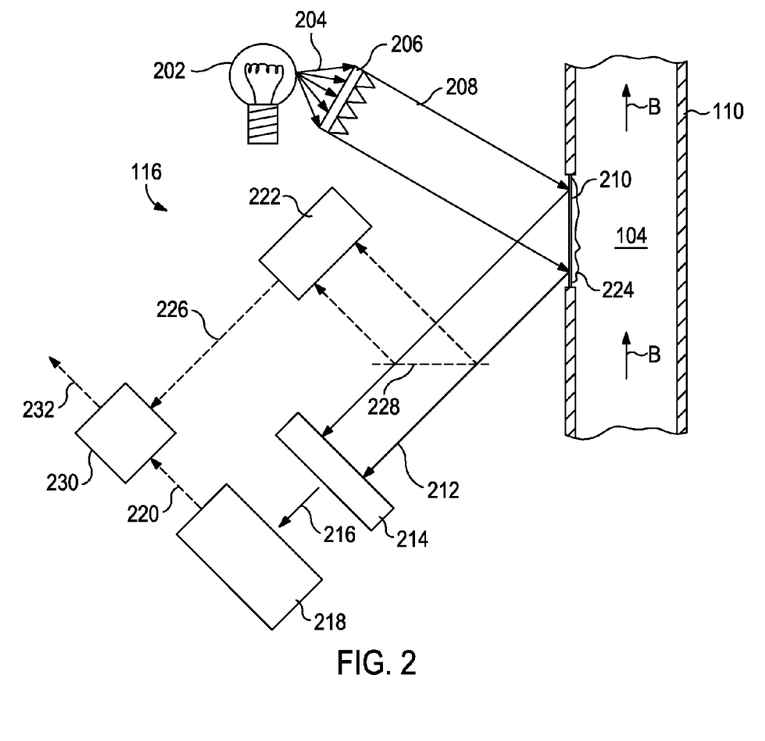
FIG. 2 illustrates an exemplary optical computing device that may be used in the inline optical fluid analyzer of FIG. 1, according to one or more embodiments.

Referring now to FIG. 2, with continued reference to FIG. 1, illustrated is an exemplary embodiment of the optical computing device 116, according to one or more embodiments. The optical computing device 116 may be representative of one or both of the first and second optical computing devices 116a,b of FIG. 1. As such, the optical computing device 116 may be coupled to or otherwise arranged along the flow path 110 which contains the sample flow of the fluid 104, as generally described above with reference to FIG. 1. As illustrated, the fluid 104 may be flowing in the general direction indicated by the arrows B (i.e., from upstream to downstream). As will be appreciated, portions of the flow path 110 may be arranged substantially vertical, substantially horizontal, or any directional configuration therebetween, without departing from the scope of the disclosure.

In some embodiments, the device 116 may include an electromagnetic radiation source 202 configured to emit or otherwise generate electromagnetic radiation 204. The electromagnetic radiation source 202 may be any device capable of emitting or generating electromagnetic radiation as defined herein, for example, a light bulb, a light emitting diode (LED), a laser, a blackbody, a photonic crystal, an X-Ray source, combinations thereof, or the like. In some embodiments, a lens 206 may be configured to collect or otherwise receive the electromagnetic radiation 204 and direct a beam 208 of electromagnetic radiation 204 toward the fluid 104. The lens 206 may be any type of optical device configured to transmit or otherwise convey the electromagnetic radiation 204 as desired. For example, the lens 206 may be a normal lens, a Fresnel lens, a diffractive optical element, a holographic graphical element, a mirror (e.g., a focusing mirror), a type of collimator, or any other electromagnetic radiation transmitting device known to those skilled in art. In other embodiments, the lens 206 may be omitted and the electromagnetic radiation 204 may instead be directed toward the fluid 104 directly from the electromagnetic radiation source 202.

In one or more embodiments, the device 116 may also include an optical sampling window 210 arranged adjacent to or otherwise in contact with the fluid 104 as it flows within the flow path 110. The optical sampling window 210 may be made from a variety of transparent, rigid or semi-rigid materials that are configured to allow transmission of the electromagnetic radiation 204 therethrough. For example, the optical sampling window 210 may be made of, but is not limited to, glasses, plastics, semi-conductors, oxides (e.g., aluminum oxide, silicon oxide, etc.), crystalline materials, polycrystalline materials, hot or cold-pressed powders, combinations thereof, or the like. After passing through the optical sampling window 210, the electromagnetic radiation 204 impinges upon and optically interacts with the fluid 104, including any components or substances present therein. As a result, optically interacted radiation 212 is generated by and reflected from the fluid 104. The optically interacted radiation 212 may alternatively be generated through transmission, scattering, diffraction, absorption, emission, or re-radiation by and/or from the fluid 104, without departing from the scope of the disclosure.

The optically interacted radiation 212 generated by the interaction with the fluid 104 may be directed to or otherwise be received by a processing element, such as an integrated computational element ("ICE") 214 arranged within the device 116. The ICE 214 is a spectral component capable of distinguishing electromagnetic radiation related to the characteristic of interest from electromagnetic radiation related to other components of the fluid 104. The ICE 214 may include a plurality of alternating layers, such as silicon (Si) and $SiO_2$ (quartz), respectively. In general, these layers consist of materials whose index of refraction is high and low, respectively. Other example materials for the layers include niobia and niobium, germanium and germania, MgF, SiO, and other high and low index materials known in the art. The layers may be strategically deposited on an optical substrate, such as BK-7 optical glass, quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

The number of layers and the thickness of each layer are determined from the spectral attributes acquired from a spectroscopic analysis of a particular characteristic using conventional spectroscopic instrument and techniques which result in a spectrograph or optical spectra of the characteristic of interest. The spectrum of interest of a given characteristic typically includes any number of different wavelengths. The multiple layers exhibit different refractive indices. By properly selecting the materials of the layers and their relative thickness and spacing, the ICE 214 may be configured to selectively pass/reflect/refract predetermined fractions of electromagnetic radiation at different wavelengths. Each wavelength is given a predetermined weighting or loading factor. The thickness and spacing of the layers may be determined using a variety of approximation methods from the spectrograph of the characteristic or analyte of interest. These methods may include inverse Fourier transform (IFT) of the optical transmission spectrum and structuring the ICE 214 as the physical representation of the IFT. The approximations convert the IFT into a structure based on known materials with constant refractive indices. Further information regarding the structures and design of exemplary ICE elements (also referred to as multivariate optical elements) is provided in *Applied Optics*, Vol. 35, pp. 5484-5492 (1996) and Vol. 29, pp. 2876-2893 (1990), which is hereby incorporated by reference.

The weightings that the layers of the ICE 214 apply at each wavelength are set to the regression weightings described with respect to a known equation, or data, or spectral signature. Briefly, the ICE 214 may be configured to perform the dot product of the input light beam into the ICE 214 and a desired loaded regression vector represented by each layer for each wavelength. As a result, the output light intensity of the ICE 214 is related to the characteristic or analyte of interest. Further details regarding how the exemplary ICE 214 is able to distinguish and process electromagnetic radiation related to the characteristic or analyte of interest are described in U.S. Pat. Nos. 6,198,531; 6,529,276; and 7,920,258, previously incorporated herein by reference.

Accordingly, in operation the ICE 214 may be configured to receive the optically interacted radiation 212 and produce modified electromagnetic radiation 216 corresponding to a particular characteristic of the fluid 104. In particular, the modified electromagnetic radiation 216 is electromagnetic radiation that has optically interacted with the ICE 214, whereby an approximate mimicking of the regression vector corresponding to the characteristic of the fluid 104 is obtained. While only one ICE 214 is shown in the device 116, embodiments are contemplated herein which include the use of at least two ICE components in the device 116 configured to cooperatively determine the characteristic of interest in the fluid 104. In other embodiments, multiple optical computing devices can be placed at a single location along the flow path 110, where each optical computing device contains a unique ICE that is configured to detect a particular characteristic of interest in the fluid 104.

The modified electromagnetic radiation 216 generated by the ICE 214 may subsequently be conveyed to a detector 218 for quantification of the signal. The detector 218 may be any device capable of detecting electromagnetic radiation, and may be generally characterized as an optical transducer. In some embodiments, the detector 218 may be, but is not limited to, a thermal detector such as a thermopile or photoacoustic detector, a semiconductor detector, a piezo-electric detector, a charge coupled device (CCD) detector, a video or array detector, a split detector, a photon detector (such as a photomultiplier tube), photodiodes, combinations thereof, or the like, or other detectors known to those skilled in the art.

In some embodiments, the detector 218 may be configured to produce an output signal 220 in real-time or near real-time in the form of a voltage (or current) that corresponds to the particular characteristic of interest in the fluid 104. The voltage returned by the detector 218 is essentially the dot product of the optical interaction of the optically interacted radiation 212 with the respective ICE 214 as a function of the concentration of the characteristic of interest of the fluid 104. As such, the output signal 220 produced by the detector 218 and the concentration of the characteristic may be related, for example, directly proportional. In other embodiments, however, the relationship may correspond to a polynomial function, an exponential function, a logarithmic function, and/or a combination thereof.

In some embodiments, the device 116 may include a second detector 222, which may be similar to the first detector 218 in that it may be any device capable of detecting electromagnetic radiation. The second detector 222 may be used to detect radiating deviations stemming from the electromagnetic radiation source 202. Undesirable radiating deviations can occur in the intensity of the electromagnetic radiation 204 due to a wide variety of reasons and potentially causing various negative effects on the device 116. These negative effects can be particularly detrimental for measurements taken over a period of time. In some embodiments, radiating deviations can occur as a result of the build-up of a film or residue 224 on the optical sampling window 210 which has the effect of reducing the amount and quality of light ultimately reaching the first detector 218. Without proper compensation, such radiating deviations could result in false readings and the output signal 220 would no longer be primarily or accurately related to the characteristic of interest.

To compensate for these types of undesirable effects, the second detector 222 may be configured to generate a compensating signal 226 generally indicative of the radiating deviations of the electromagnetic radiation source 202, and thereby normalize the output signal 220 generated by the first detector 218. As illustrated, the second detector 222 may be configured to receive a portion of the optically interacted radiation 212 via a beamsplitter 228 in order to detect the radiating deviations. In other embodiments, however, the second detector 222 may be arranged to receive electromagnetic radiation from any portion of the optical train in the device 116 in order to detect the radiating deviations, without departing from the scope of the disclosure.

In some applications, the output signal 220 and the compensating signal 226 may be conveyed to or otherwise received by a signal processor 230 communicably coupled to both the detectors 220, 228. The signal processor 230 may be a computer including a processor and a machine-readable storage medium having instructions stored thereon, which, when executed by the processor 230, cause the optical computing device 116 to perform a number of operations, such as determining a characteristic of interest of the fluid 104. For instance, the concentration of each characteristic detected with the optical computing device 116 can be fed into an algorithm operated by the signal processor 230. The algorithm can be part of an artificial neural network configured to use the concentration of each detected characteristic in order to evaluate the overall characteristic(s) or quality of the fluid 104. Illustrative but non-limiting artificial neural networks are described in commonly owned U.S. patent application Ser. No. 11/986,763 (U.S. Patent App. Pub. No. 2009/0182693), which is incorporated herein by reference.

The signal processor 230 may also be configured to computationally combine the compensating signal 226 with the output signal 220 in order to normalize the output signal 220 in view of any radiating deviations detected by the second detector 222. Computationally combining the output and compensating signals 220, 226 may entail computing a ratio of the two signals 220, 226. For example, the concentration or magnitude of each characteristic determined using the optical computing device 116 can be fed into an algorithm run by the signal processor 230. The algorithm may be configured to make predictions on how the characteristics of the fluid 104 change if the concentrations of one or more components or additives are changed relative to one another.

In real-time or near real-time, the signal processor 230 may be configured to provide a resulting output signal 232 corresponding to a concentration of the characteristic of interest in the fluid 104. The resulting output signal 232 may be readable by an operator who can consider the results and make proper adjustments or take appropriate action, if needed, based upon the measured concentrations of chemical compounds in the fluid 104. In some embodiments, the resulting signal output signal 232 may be conveyed, either wired or wirelessly, to the operator for consideration.

Figure 3:
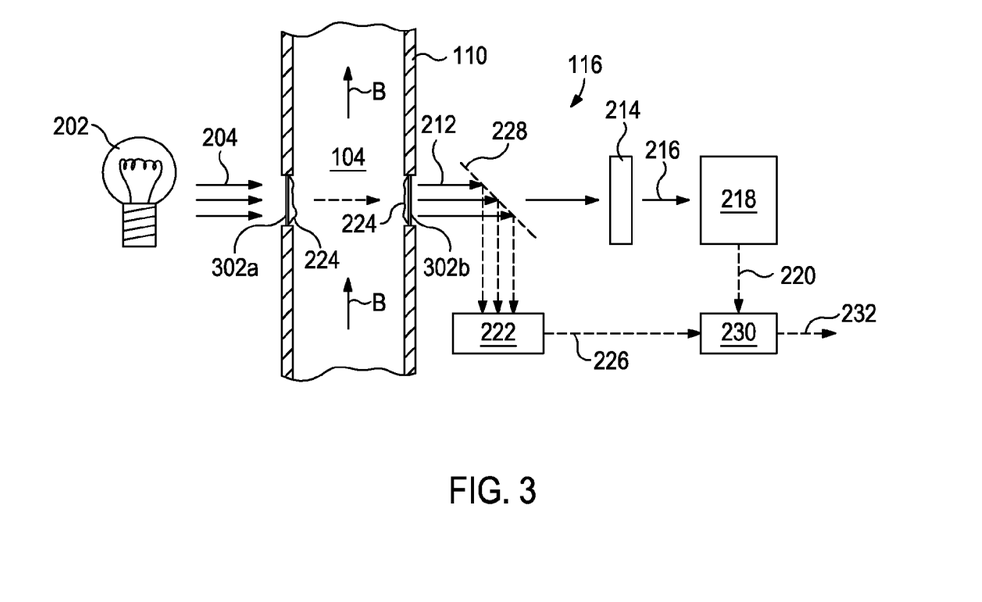
FIG. 3 illustrates another exemplary optical computing device that may be used in the inline optical fluid analyzer of FIG. 1, according to one or more embodiments.

Referring now to FIG. 3, illustrated is another exemplary embodiment of the optical computing device 116, according to one or more embodiments. As with the optical computing device 116 of FIG. 2, the optical computing device 116 in FIG. 3 may be representative of one or both of the first and second optical computing devices 116a,b of FIG. 1. The optical computing device 116 may be best understood with reference to the optical computing device 116 of FIG. 2, where like numerals indicate like elements that will not be described again. Unlike the device 116 of FIG. 2, however, the optical computing device 116 in FIG. 3 may be configured to transmit the electromagnetic radiation 204 through the fluid 104 via a first optical sampling window 302a and a second optical sampling window 302b arranged radially-opposite the first optical sampling window 302a in the flow path 110. The first and second optical sampling windows 302a,b may be similar to the optical sampling window 210 described above in FIG. 2, and therefore will not be described in greater detail.

As the electromagnetic radiation 204 passes through the fluid 104 via the first and second optical sampling windows 302a,b, it optically interacts with the fluid 104 and optically interacted radiation 212 is subsequently directed to or otherwise received by the ICE 214 as arranged within the device 116. While FIG. 3 depicts the ICE 214 as receiving the optically interacted radiation 212 as transmitted through the optical sampling windows 302a,b, the ICE 214 may equally be arranged at any point along the optical train of the device 116, without departing from the scope of the disclosure.

The modified electromagnetic radiation 216 generated by the ICE 214 is subsequently conveyed to the detector 218 for quantification of the signal and generation of the output signal 220 which corresponds to the particular characteristic of interest in the fluid 104. The device 116 may also include the second detector 222 for detecting radiating deviations stemming from the electromagnetic radiation source 202. In at least one embodiment, the radiating deviations may be derived from the build up of the residue 224 on one or both of the optical sampling windows 302a,b. As illustrated, the second detector 222 may be configured to receive a portion of the optically interacted radiation 212 via the beamsplitter 228 in order to detect the radiating deviations. The output signal 220 and the compensating signal 226 may then be conveyed to or otherwise received by the signal processor 230 which may computationally combine the two signals 230, 226 and provide in real-time or near real-time the resulting output signal 232 corresponding to a normalized concentration of the characteristic of interest in the fluid 104.

Referring again to FIG. 1, with continued reference to FIGS. 2 and 3, the inline fluid analyzer 100 may further include a window cleaning system 118 fluidly coupled thereto. Specifically, the window cleaning system 118 may include a solvent dispenser 120 fluidly coupled to the inlet 108a of the sampling module 106 via a third conduit 122. The solvent dispenser 120 may store or otherwise house one or more solvents configured to be injected into the flow path 110 via the third conduit 122. As discussed in greater detail below, the solvent used in the window cleaning system 118 may be configured to clean the optical sampling windows of the optical computing devices 116a,b, such as the optical sampling window 210 of FIG. 2 and/or the optical sampling windows 302a,b of FIG. 3.

As briefly discussed above, the optical sampling windows 210, 302a,b may, over time, develop a film or residue 224 (FIGS. 2 and 3) thereon. The residue 224 may be a build up of one or more substances or chemical constituents present in the fluid 104 which tend to coalesce on the surfaces of the optical sampling windows 210, 302a,b that are in direct contact with the fluid 104. The residue 224 may be, for example, a build up of asphaltenes, waxes, paraffins, olefins, esters (e.g., oil-based mud residuals), aromatics, methane, C1-C5 hydrocarbons, saturates, foams, salts, particulates, sand, or combinations thereof. The residue 224 may adversely affect the signal quality of the output signal 220 (FIGS. 2 and 3) from each optical computing device 116a,b. For instance, as the residue 224 develops, the resulting optical spectra and/or regression vectors provided by the output signal 220 are distorted or otherwise skewed and thereby report inaccurate readings. As a result, the operator is provided with erroneous data regarding the particular characteristic(s) being measured in the fluid 104 with the optical computing devices 116a,b.

While in some applications the variations in the output signal 220 may be substantially normalized through the use of the second detector 222 (FIGS. 2 and 3) and its compensating signal 226, as generally discussed above, it is nonetheless desirable to remove the residue 224 in order to obtain a cleaner output signal 220. If not, the optical computing devices 116a,b may have to be recalibrated periodically to account for the variations in the optical signals resulting from the residue 224. Such a process can be time-consuming and add additional complexity to the operations.

In exemplary operation, the window cleaning system 118 may be initiated or otherwise engaged by closing a first valve 124 arranged in the first conduit 112, thereby shutting off the sample flow of the fluid 104 through the flow path 110 of the sampling module 106. Simultaneously, or otherwise just after closing the first valve 124, a second valve 126 arranged in the third conduit 122 may be opened, thereby providing a flow of solvent from the solvent dispenser 120 into the flow path 110 via the inlet 108a. The valves 124, 126 may be any type of isolation valve including, but not limited to, gate valves, knife valves, or the like. Moreover, the valves 124, 126 may be actuated either manually or mechanically. For instance, the valves may be mechanically actuated with one or more mechanical or electro-mechanical actuation devices, solenoids or actuators, and may be powered via hydraulics, electricity, and/or pneumatics. The valves 124, 126 may also be either locally or remotely operated via one or more wired or wireless communication technologies. Accordingly, in at least one embodiment, actuation of the valves 124, 126 may be automated.

The solvent may be configured to react with the residue 224 on the optical sampling windows 210, 302a,b (FIGS. 2 and 3) of the optical computing devices 116a,b. In particular, the solvent may react with and dissolve any foreign particles in the residue 224, thereby substantially or entirely clearing the residue 224 from the exposed surface of the optical sampling windows 210, 302a,b. In some embodiments, the solvent may be toluene. In other embodiments, however, the solvent may be any type of solvent configured to react with the residue 224 such as, but not limited to, butanone (i.e., methyl ethyl ketone or MEK), xylene, any organic solvents, any inorganic solvents, combinations thereof, or the like.

Examples of organic solvents that may be used include acetic acid, acetone, acetonitrile, benzene, 1-butanol, 2-butanol, t-butyl alcohol, carbon tetrachloride, chlorobenzene, chloroform, cyclohexane, 1,2-dichloroethane, diethyl ether, diethylene glycol, diglyme (diethylene glycol dimethyl ether), 1,2-dimethoxy-ethane (glyme, DME), dimethylether, dimethyl-formamide (DMF), dimethyl sulfoxide (DMSO), dioxane, ethanol, ethyl acetate, ethylene glycol, glycerin, heptane, hexamethylphosphoramide (HMPA), hexamethylphosphorous triamide (HMPT), hexane, methanol, methyl t-butyl ether (MTBE), methylene chloride, N-methyl-2-pyrrolidinone (NMP), nitromethane, pentane, Petroleum ether (ligroine), 1-propanol, 2-propanol, pyridine, tetrahydrofuran (THF), triethyl amine, o-xylene, m-xylene, p-xylene, and the like.

Spent solvent is eventually discharged from the sampling module 106 at the outlet 108b and conveyed to the pipeline 102 via the second conduit 114 where it joins the main flow of the fluid 104. The spent solvent may be subsequently removed from the fluid 104 at a downstream location using one or more separation processes generally known by those skilled in the art. In other embodiments, however, the spent solvent may be discharged from the sampling module 106 and conveyed back to the solvent dispenser 120 via a fourth conduit 128 (shown in dashed). In such an embodiment, the solvent dispenser 120 may be configured to rehabilitate or otherwise clean the solvent in preparation for recirculating the solvent back through the sampling module 106. As will be appreciated, the inline fluid analyzer 100 may have one or more additional valves (not shown) configured to divert the spent solvent to the solvent dispenser 120.

When it is desired to conclude the window cleaning treatment using the window cleaning system 118, the second valve 126 may once again be closed, thereby shutting off the influx of solvent into the flow path 110 of the sampling module 106. Simultaneously, or otherwise just after closing the second valve 126, the first valve 124 may be reopened in order to resume the sample flow of the fluid 104 through the flow path 110. The optical computing devices 116a,b may then resume monitoring the fluid 104 for particular characteristics.

In some embodiments, the window cleaning treatment may be initiated or otherwise undertaken on a predetermined schedule or at predetermined times. For instance, it may be advantageous to run the window cleaning system 118 every week, every two weeks, once a month, etc., in order to provide a periodic and planned cleansing of the optical sampling windows 210, 302a,b.

In other embodiments, however, window cleaning treatments may be initiated or otherwise carried out when the signal quality of the output signal 220 (FIGS. 2 and 3) from one or both of the optical computing devices 116a,b reports increased concentrations of a substance or otherwise surpasses a predetermined quality or concentration threshold. For example, the ICE 214 (FIGS. 2 and 3) in one or both of the optical computing devices 116a,b may be configured to monitor a particular chemical compound or constituent within the fluid 104, such as asphaltenes. As such, the output signal 220, in the form of an optical spectra and/or regression vector, may correspond to the relative concentration of asphaltenes in the fluid 104. Variations in the resulting optical spectra and/or regression vector, such as increased or extended amplitudes, may be an indication of either an increased flow of asphaltenes in the fluid 104 or a build up of an asphaltene residue 224 on the optical sampling windows 210, 302a,b.

If, after completing a window cleaning treatment, the optical spectra and/or regression vector does not return to normal amplitudes, this may be an indication that the fluid 104 contains an above-normal concentration of asphaltenes. However, if the optical spectra and/or regression vector does return to normal amplitudes, this may be an indication that the regression vector anomaly was the result of a build up of residue 224 consisting primarily of asphaltenes. As will be appreciated, the optical computing devices 116a,b may include multiple ICEs 214 configured to monitor multiple characteristics. As a result, when a change in the regression vector for any of these ICE 214 is reported, a window cleaning treatment may be undertaken to determine if the anomaly in the output signal(s) 220 is the result of residue 2240 on the optical sampling windows 210, 302a,b or otherwise an increased flow or concentration of that particular chemical constituent in the fluid 104.

In yet other embodiments, the window cleaning treatment may be initiated or otherwise carried out when the signal quality of the output signal 220 is irregular or otherwise varied from normal. For instance, when the quality of the resulting optical spectra and/or regression vector provided by the output signal 220 degrades or otherwise becomes irregular, this may be either an indication of a build up of residue 224 on the optical sampling windows 210, 302a,b or otherwise in increased concentration of an unknown or non-monitored substance within the fluid 104. If, after completing a window cleaning treatment, the optical spectra and/or regression vector returns to normal amplitudes, this may be an indication that residue 224 was the source of the degrading signal quality and that the cleaning treatment was successful. If, however, the optical spectra and/or regression vector does not return to normal following a cleaning treatment, an additional window cleaning treatment may be required. If the additional window cleaning treatment(s) was not successful in bringing the regression vector readings back to normal, the optical computing devices 116a,b may be recalibrated to take into account the offset variation, thereby providing the user with accurate readings corresponding to the characteristic of interest.

In some embodiments, the window cleaning treatment(s) may be manually initiated by the user when needed. In other embodiments, however, the window cleaning system 118 may fully automated. For instance, the window cleaning system 118 may be communicably coupled to a computer or the like which reads or otherwise receives the output signal(s) 220. When an output signal 220 surpasses a predetermined threshold, the computer may be configured to send an alert to the operator of the threshold breach or otherwise automatically actuate the valves 124, 126 in order to commence a window cleaning treatment.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), electrically erasable programmable read only memory (EEPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

In some embodiments, the data collected using the optical computing devices can be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system can also allow remote monitoring and operation of a process to take place. Automated control with a long-range communication system can further facilitate the performance of remote job operations. In particular, an artificial neural network can be used in some embodiments to facilitate the performance of remote job operations. That is, remote job operations can be conducted automatically in some embodiments. In other embodiments, however, remote job operations can occur under direct operator control, where the operator is not at the job site.

It should also be noted that the various drawings provided herein are not necessarily drawn to scale nor are they, strictly speaking, depicted as optically correct as understood by those skilled in optics. Instead, the drawings are merely illustrative in nature and used generally herein in order to supplement understanding of the systems and methods provided herein. Indeed, while the drawings may not be optically accurate, the conceptual interpretations depicted therein accurately reflect the exemplary nature of the various embodiments disclosed.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein.

Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. An inline optical fluid analyzer, comprising:
    a sampling module having an inlet and an outlet and a flow path extending therebetween, the flow path being fluidly coupled to a pipeline containing a fluid;
    at least one optical computing device arranged within the sampling module in optical communication with the flow path and configured to monitor a sample flow of the fluid for one or more characteristics of the fluid, the at least one optical computing device having one or more optical sampling windows in contact with the sample flow of the fluid; and
    a solvent dispenser fluidly coupled to the flow path and configured to provide a solvent to the flow path to remove a residue built up on the one or more sampling windows, wherein the solvent dispenser is configured to provide the solvent to the flow path when the sample flow of the fluid is shut off.

2. The inline optical fluid analyzer of claim 1, wherein the fluid is a hydrocarbon.

3. The inline optical fluid analyzer of claim 1, wherein the fluid is an aqueous fluid.

4. The inline optical fluid analyzer of claim 1, further comprising:
    a first conduit fluidly coupling the pipeline to the inlet of the flow path, the first conduit being configured to convey the sample flow of the fluid to the flow path;
    a second conduit fluidly coupling the pipeline to the outlet of the flow path; and
    a third conduit fluidly coupling the solvent dispenser to the inlet of the flow path, the third conduit being configured to convey the solvent to the flow path.

5. The inline optical fluid analyzer of claim 4, further comprising:
    a first valve arranged in the first conduit and configured to control the sample flow of the fluid into the flow path; and
    a second valve arranged in the third conduit and configured to regulate a flow of the solvent into the flow path.

6. The inline optical fluid analyzer of claim 5, wherein one or both of the first and second valves are mechanically actuated.

7. The inline optical fluid analyzer of claim 1, wherein the optical computing device comprises:
    at least one integrated computational element configured to optically interact with the sample flow of the fluid and thereby generate optically interacted light; and
    at least one detector arranged to receive the optically interacted light and generate an output signal corresponding to the one or more characteristics of the fluid.

8. The inline optical fluid analyzer of claim 7, wherein the optical computing device further comprises an electromagnetic radiation source configured to emit electromagnetic radiation that optically interacts with the sample flow of the fluid.

9. The inline optical fluid analyzer of claim 1, wherein the one or more characteristics of the fluid comprise a concentration of a chemical composition present within the fluid.

10. The inline optical fluid analyzer of claim 9, wherein the chemical composition includes at least one of paraffins, waxes, asphaltenes, aromatics, methane, olefins, esters, C1-C5 hydrocarbons, saturates, foams, salts, particulates, and sand.

11. The inline optical fluid analyzer of claim 1, wherein the solvent comprises at least one of toluene, butanone, xylene, any organic solvent, any inorganic solvent, and any combination of the foregoing.

12. A method of operating an inline optical fluid analyzer, comprising:
    directing a sample flow of a fluid to a flow path defined within a sampling module having an inlet and an outlet, the flow path extending between the inlet and the outlet;
    analyzing the sample flow of the fluid for one or more characteristics with at least one optical computing device arranged within the sampling module and having one or more optical sampling windows in contact with the sample flow of the fluid;
    shutting off the sample flow of the fluid to the flow path for cleaning the sampling module;
    providing a solvent to the flow path from a solvent dispenser fluidly coupled to the inlet; and
    at least partially removing a residue built up on the one or more sampling windows with the solvent.

13. The method of claim 12, wherein directing the sample flow of the fluid to the flow path further comprises:
    conveying the sample flow of the fluid from a pipeline containing the fluid via a first conduit that fluidly couples the pipeline to the inlet of the flow path;
    directing the sample flow of the fluid through the flow path; and
    discharging the sample flow of the fluid from the flow path and back into the pipeline via a second conduit that fluidly couples the outlet to the pipeline.

14. The method of claim 13, further comprising:
    closing a first valve arranged in the first conduit for shutting off the sample flow of the fluid to the flow path; and
    opening a second valve arranged in a third conduit, the third conduit fluidly coupling the solvent dispenser to the inlet of the flow path for providing the solvent to the flow path.

15. The method of claim 14, further comprising mechanically actuating one or both of the first and second valves.

16. The method of claim 14, further comprising:
closing the second valve and thereby stopping a flow of the solvent into the flow path;
opening the first valve and thereby directing the sample flow of the fluid back into the flow path; and
resuming an analysis of the sample flow of the fluid with the at least one optical computing device.

17. The method of claim 12, further comprising generating an output signal corresponding to the one or more characteristics of the fluid with the at least one optical computing device, the at least one optical computing device having at least one integrated computational element configured to optically interact with the sample flow of the fluid and convey optically interacted light to a detector which generates the output signal.

18. A method of cleaning an inline optical fluid analyzer, comprising:
flowing a fluid through a flow path defined in a sampling module having an inlet and an outlet, the flow path extending between the inlet and the outlet;
analyzing the fluid with at least one optical computing device arranged in optical communication with the fluid and having one or more optical sampling windows in contact with the fluid;
providing an output signal corresponding to one or more characteristics of the fluid with the at least one optical computing device;
shutting off a flow of the fluid to the sampling module; and
initiating a window cleaning treatment by providing a solvent to the flow path to remove a residue built up on the one or more sampling windows, the solvent being injected into the flow path from a solvent dispenser fluidly coupled to the inlet.

19. The method of claim 18, further comprising:
closing a first valve arranged in a first conduit fluidly coupling a pipeline to the flow path, thereby shutting off the flow of the fluid to the sampling module; and
opening a second valve arranged in a second conduit, the second conduit fluidly coupling the solvent dispenser to the inlet.

20. The method of claim 18, further comprising initiating the window cleaning treatment when a signal quality of the output signal degrades or when the output signal reports an increased concentration of the one or more characteristics.

21. The method of claim 18, further comprising:
resuming a flow of the fluid through the flow path following the window cleaning treatment;
resuming an analysis of the fluid with the at least one optical computing device; and
determining whether the residue was removed by the solvent with the at least one optical computing device.

* * * * *